United States Patent [19]

Griffin et al.

[11] 4,441,917

[45] Apr. 10, 1984

[54] HERBICIDAL UREA DERIVATIVES

[75] Inventors: David A. Griffin, Bracknell; David J. Collins, Crowthorne, both of England

[73] Assignee: Imperial Chemical Industries PLC, London, England

[21] Appl. No.: 381,888

[22] Filed: May 25, 1982

[30] Foreign Application Priority Data

Jun. 9, 1981 [GB] United Kingdom ............... 8117680

[51] Int. Cl.³ ................. A01N 41/06; C07C 143/833
[52] U.S. Cl. ................... 71/103; 260/465 D; 560/13
[58] Field of Search ............ 260/465 D; 560/13; 71/103

[56] References Cited

U.S. PATENT DOCUMENTS 3,547,618 12/1970 Speziale et al. .............. 71/103
3,799,760 3/1970 Stephens ..................... 71/103
4,230,874 10/1980 Pallos et al. ................. 560/12

FOREIGN PATENT DOCUMENTS 52856 6/1982 European Pat. Off. .

OTHER PUBLICATIONS

Bretschneider et al., Monatsheft fur Chemie, vol. 103, pp. 1396-1397 (1972).

*Primary Examiner*—Dolph H. Torrence
*Attorney, Agent, or Firm*—Cushman, Darby & Cushman

[57] ABSTRACT

Sulphonyl urea derivatives of formula

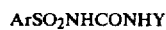

wherein Ar is an optionally substituted phenyl ring and Y is $-CO_2R^1$, $-CONR^2R^3$,

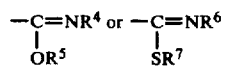

wherein $R^1$ to $R^7$ are H, or optionally substituted aliphatic or phenyl radicals. These derivatives are useful as herbicides e.g. for cereals.

17 Claims, No Drawings

HERBICIDAL UREA DERIVATIVES

According to the present invention, there are provided sulphonyl urea compounds of the formula (I)

$$ArSO_2NHCONHY \qquad (I)$$

wherein Ar is a phenyl ring optionally bearing from one to five substituents which may be the same or different, and Y is (a) a group $—CO_2R^1$ wherein $R^1$ is an optionally substituted alkyl, alkenyl, alkynyl, or phenyl group; (b) a group $—CONR^2R^3$ wherein $R^2$ is hydrogen or an optionally substituted alkyl, alkenyl, alkynyl, or phenyl group, and $R^3$ is hydrogen, or an optionally substituted alkyl, alkenyl, alkynyl or phenyl group or $R^2$ and $R^3$ together with the nitrogen atom to which they are attached form a heterocyclic ring; (c) a group

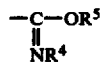

wherein each group $R^4$ and $R^5$ is a hydrogen atom or an optionally substituted alkyl, alkenyl, alkynyl or phenyl group; or (d) a group

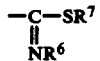

wherein each group $R^6$ and $R^7$ is a hydrogen atom or an optionally substituted alkyl, alkenyl, alkynyl, or phenyl group; and salts thereof.

As defined above, the invention includes compounds in which Ar is an unsubstituted phenyl ring, or a phenyl ring containing 1 to 5 substituents.

The invention thus includes compounds in which Ar is a phenyl ring having 1, 2 or 3 substituents. Where only 1 or 2 substituents are present they may be for example located in the 2- or the 2- and 6-positions of the phenyl ring, although the invention also includes compounds wherein the substituents are located elsewhere in the phenyl ring.

The substituent or substituents present in the group Ar may include, for example, halogen (ie fluorine, chlorine, bromine and iodine), alkyl (eg alkyl of 1 to 4 carbon atoms, haloalkyl (eg fluoro- and chloroalkyl of 1 to 4 carbon atoms, for example $CF_3$), alkoxy (eg $C_1$–$C_4$ alkoxy), alkylthio (eg $C_1$–$C_4$ alkylthio), alkyl sulphinyl and alkylsulphonyl (each of 1 to 4 carbon atoms, for example) carboxyl and salts thereof, alkoxycarbonyl (eg $C_2$–$C_5$ alkoxycarbonyl), carbamoyl, N-substituted carbamoyl (eg mono- and di-methyl and ethyl carbamoyl), cyano, nitro, amino, and mono- and di-alkylamino (eg wherein the one or two alkyl groups each have 1 to 4 carbon atoms).

A sub-class of the foregoing compounds comprises those compounds in which Ar is a 2-substituted phenyl group; for example 2-methoxyphenyl, 2-cyanophenyl, 2-halophenyl, 2-chloromethylphenyl, 2-bromomethylphenyl, 2-methylthiophenyl, 2-methylsulphinylphenyl, 2-methylsulphonylphenyl, 2-aminophenyl, 2-methylaminophenyl, 2-dimethylaminophenyl, 2-trifluoromethylphenyl, 2-carbamoylphenyl and 2-methoxycarbonylphenyl. The 2-halophenyl compounds include, in particular, 2-chlorophenyl.

A further subclass comprises those compounds which have both a 2- and a 6-substituent; for example 2,6-dihalophenyl compounds, e.g. 2,6-dichlorophenyl compounds.

A separate sub-class comprises compounds which have a 4-nitro-substituent in the phenyl ring of the Ar group.

When any of the groups $R^1$ to $R^7$ is an optionally substituted alkyl, alkenyl or alkynyl group, it may for example contain from 1 to 6 carbon atoms in the case of an alkyl group and from 2 to 6 carbon atoms in the case of an alkenyl or alkynyl group. Thus, for example, when the group Y is a $—CO_2R^1$ group, the $R^1$ group may be for example an alkyl group of 1 to 3 carbon atoms (e.g. an ethyl group) or an allyl group.

When any of the groups $R^1$ to $R^7$ is substituted alkyl, alkenyl, alkynyl, or phenyl group, there may be one or more substituents. Examples of substituents include, inter alia, those listed above as examples of substituents for the group Ar. When $R^2$ and $R^3$ together with the nitrogen atom to which they are attached form a heterocyclic ring, the ring may be, for example, a pyrrolidine, piperidine, or morpholine ring.

Particular examples of compounds according to the invention are listed in Table I below:

| Compound No | Ar | Y | Melting Point °C. |
|---|---|---|---|
| 1 | 2-Cl.C$_6$H$_4$. | C$_2$H$_5$OCO | 118–119 |
| 2 | 2-Cl.C$_6$H$_4$. | isoC$_3$H$_7$OCO | 139–141 |
| 3 | 2-Cl.C$_6$H$_4$. | CH$_3$OCO | 144–146 |
| 4 | 2-Cl.C$_6$H$_4$. | C$_6$H$_5$OCO | 133–135 |
| 5 | 4-CH$_3$.C$_6$H$_4$ | C$_2$H$_5$OCO | 172 |
| 6 | 4-Cl.C$_6$H$_4$. | C$_2$H$_5$OCO | 143 |
| 7 | 2-Cl—5-NO$_2$.C$_6$H$_3$. | C$_2$H$_5$OCO | 158–159 |
| 8 | 2-Cl.C$_6$H$_4$. | C$_6$H$_5$CH$_2$OCO | 166–169 |
| 9 | C$_6$H$_5$. | C$_2$H$_5$OCO | 165.5 |
| 10 | 2-CH$_3$OCO.C$_6$H$_4$. | C$_2$H$_5$OCO | 158–160 |
| 11 | 3-CH$_3$.C$_6$H$_4$. | C$_2$H$_5$OCO | 75 |
| 12 | 2,5-Cl$_2$.C$_6$H$_3$. | C$_2$H$_5$OCO | 152–153 |
| 13 | 4-CH$_3$O.C$_6$H$_4$. | C$_2$H$_5$OCO | 154 |
| 14 | 2-Cl.C$_6$H$_4$. | C$_3$H$_7$OCO | 79–82 |
| 15 | 2-Cl.C$_6$H$_4$. | CH$_3$OCH$_2$CH$_2$OCO | 132–135 |
| 16 | 2-F.C$_6$H$_4$. | C$_2$H$_5$OCO | 113–115 |
| 17 | 2-NO$_2$.C$_6$H$_4$. | C$_2$H$_5$OCO | 132 |
| 18 | 3,4-Cl$_2$.C$_6$H$_3$ | C$_2$H$_5$OCO | 142 |
| 19 | 3,4-(CH$_3$)$_2$.C$_6$H$_3$. | C$_2$H$_5$OCO | 119 |
| 20 | 2,4,6-Cl$_3$.C$_6$H$_2$. | C$_2$H$_5$OCO | 166–167 |
| 21 | 2,4,6-Br$_3$.C$_6$H$_2$. | C$_2$H$_5$OCO | 175–176 |
| 22 | 2,6-Cl$_2$.C$_6$H$_3$. | C$_2$H$_5$OCO | 168–169 |
| 23 | 3-NO$_2$.C$_6$H$_4$. | C$_2$H$_5$OCO | 146 |
| 24 | 4-t-Bu.C$_6$H$_4$. | C$_2$H$_5$OCO | 139 |
| 25 | 2-CF$_3$.C$_6$H$_4$. | C$_2$H$_5$OCO | 132–134 |
| 26 | 2-Br.C$_6$H$_4$. | C$_2$H$_5$OCO | 149 |
| 27 | 2-Cl.C$_6$H$_4$. | CH$_2$=CHCH$_2$OCO | 75–85 (decomp) |
| 28 | 2-CH$_3$O—3-Cl.C$_6$H$_3$. | C$_2$H$_5$OCO | 135–136 |
| 29 | 4-NO$_2$.C$_6$H$_4$ | C$_2$H$_5$OCO | 190 |
| 30 | 4-F.C$_6$H$_4$ | C$_2$H$_5$OCO | 167 |

The hydrogen atom in the $—SO_2NH—$ group of the compounds of formula (I) is acidic, and the compounds form salts with bases. These salts may be prepared by the usual procedures known to those skilled in the art for preparing salts from acids. Examples of salts include metal salts, for example salts of alkali metal or alkaline earth metal cations, including for example salts of sodium, potassium, lithium, calcium and magnesium cations. Other examples of salts include those formed from ammonium and substituted ammonium cations. Substituted ammonium cations include for example cations in which one, two, three or four of the hydrogen atoms of the ammonium cation are replaced by an optionally substituted alkyl radical. Particular examples of substituted ammonium cations include methyl-, ethyl-, propyl-, isopropyl-, benzyl-, dimethyl-, diethyl-, 2-hydroxyethyl-, bis (2-hydroxyethyl)-, trimethyl-, triethyl-, tetramethyl-, tetraethyl- and benzyltrimethylammonium.

The invention further provides processes for preparing compounds of formula (I) above. One such process is outlined in Scheme A below:

Scheme A

According to Scheme A, an appropriately substituted amino derivative $NH_2Y$ is reacted with an arylsulphonylisocyanate $ArSO_2NCO$, preferably in the presence of a basic catalyst to give the required compound of formula (I). Preferably the reaction is carried out in an inert diluent or solvent. Examples of such solvents include halogenated hydrocarbons, for example dichloromethane, and polar aprotic solvents, for example acetonitrile. The solvent or diluent should be dried before use to avoid loss of the isocyanate reactant by reaction with traces of water present in the solvent. Generally the reaction proceeds at a convenient rate at room temperature (i.e. 20°-30° C.), but heating may be applied (eg to 50°-100° C.) to accelerate the reaction if desired. The basic catalyst is preferably a tertiary amine, for example diazabicycloctane (DABCO) or 4-dimethylaminopyridine. Usually the reactants are employed in stoichiometric proportions. The product is isolated by conventional methods. Thus if the product precipitates from the reaction solution it is filtered off, washed with solvent, and dried. If it remains in solution, then the solution is concentrated under reduced pressure to yield the crude solid product. If desired, the product may be further purified by recrystallisation. Dichloromethane and carbon tetrachloride are solvents that are often useful for this purpose.

In an alternative process for preparing the compounds of the invention, an arylsulphonamide is reacted in the form of its metal salt with an appropriate isocyanate as shown in Scheme B below:

Scheme B

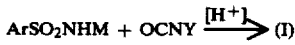

In Scheme B, the symbol M stands for an alkali metal, for example sodium or potassium. Preferably the reaction is conducted in an inert solvent or diluent; examples of solvents include dimethylformamide, dimethylacetamide and N-methylpyrrolidinone; other aprotic solvents may also be used. The metal salt of the arylsulphonamide may be prepared by standard procedures; for example, the sulphonamide could be dissolved in the stoichiometric amount of a solution of sodium or potassium hydroxide or carbonate and the solution evaporated to give the required salt, which could then be dried for use in the reaction. A convenient procedure, however, is to prepare the sodium salt of the sulphonamide in the reaction medium itself, by treating a solution of the sulphonamide with an equimolar proportion of sodium hydride. When evolution of hydrogen has ceased, the suspension of the sodium salt is stirred and treated with the isocyanate. The reaction usually proceeds reasonably quickly at ambient temperatures (i.e. 20°-30° C.) and may be complete in a period of from 5 minutes to 16 hours. At the end of the reaction period, the mixture may be diluted with water and acidified. The product may be isolated by conventional methods; for example, the acidified diluted reaction mixture may be extracted with an organic solvent (e.g. ethyl acetate). The extracts may then be washed with saturated sodium bicarbonate solution. The bicarbonate washings may then be acidified to liberate the free sulphonamide. Usually this precipitates, and may be collected, washed, dried and purified further (e.g. by recrystallisation) if desired.

In some cases it may be preferable to carry out the reaction of Scheme B using the free sulphonamide, rather than the metal salt; in these cases, a tertiary amine is added as a base to facilitate reaction and heating (e.g. to 50°-100° C.) may be applied to accelerate the reaction. The tertiary amine may be an aliphatic amine e.g. triethylamine and is preferably added in at least an equimolar proportion with respect to the arylsulphonamide.

The arylsulphonamides used in Scheme B are in many cases known compounds. Where an individual compound has not been reported in the chemical literature it may be prepared by known procedures. Usually the sulphonamide is prepared by reacting the corresponding arylsulphonyl chloride with concentrated ammonia. Procedures for preparing arylsulphonamides are described by Crossley et al, Journal of the American Chemical Society, 1938, volume 60, p. 2223, and P. A. Rossy et al, Journal of Organic Chemistry, 1980 volume 45, p.617, the disclosures of which are herein incorporated by reference. By way of example, the preparation of 2-chlorobenzenesulphonamide is described below:

2-Chlorobenzenesulphonyl chloride (58 g) in either (60 ml) was added dropwise with stirring to concentrated ammonia solution (575 ml). When addition was complete, the mixture was stirred and heated at 70° C. for 1 hour. The mixture was then cooled and the solid filtered off, washed with water, and dried to give the required 2-chlorobenzenesulphonamide (39 g) with a melting point of 186° C.

The arylsulphonyl chlorides, where not commercially available, were made from the corresponding aniline derivatives, by diazotisation and treatment of the diazonium salts with sulphur dioxide in the presence of cupric chloride. Procedures for preparing arylsulphonyl chlorides are described by H. L. Yale and F. Sowinski in the Journal of Organic Chemistry, 1960, volume 25, at p.1824, and by Meerwein et al, J.prakt.Chem., 1939, volume 152, p.251, the disclosures of which are hereby incorporated by reference. By way of a particular example, the preparation of 2-chlorobenzenesulphonyl chloride is described below:

o-Chloroaniline (51.0 g) was dissolved in a mixture of concentrated hydrochloric acid (140 ml) and glacial acetic acid (40 ml) and cooled to 0° C. with stirring while a solution of sodium nitrite (27.6 g) with water (60 ml) was added slowly. When addition was complete, the mixture was stirred for 10 minutes and then added to a saturated solution of sulphur dioxide in glacial acetic acid (540 ml) containing cupric chloride (8 g) and kept at 0° C. The mixture was allowed to warm to room temperature and then poured into ice and water, and extracted with ether. The ether extracts were evaporated to give an oil which was distilled. The fraction of boiling point 97°-102° C./0.1 Torr (58 g) was collected and identified as 2-chlorobenzenesulphonyl chloride.

The isocyanates YNCO are known compounds or may be prepared by conventional methods. The arylsulphonylisocyanates used as starting materials are in general known compounds. Where an individual arylsulphonylisocyanate has not been previously recorded in the literature, it may be prepared by conventional methods; for example by the procedures described in Newer Methods of Preparative Organic Chemistry, volume VI, article by H. Ulrich and A. A. Y. Sayigh at pages 223-241, published by Academic Press and edited by W. Foerst. The amine derivatives $NH_2Y$ are also known compounds or may be made by conventional methods.

Thus, for example, the amine derivatives $NH_2Y$ wherein Y is a —$CO_2R^1$ group may be prepared by the sequential addition of the appropriate alcohol $R^1OH$ and aqueous ammonia to phosgene in toluene according to the procedure described by H. E. Carter, R. L. Frank and H. W. Johnson, in Organic Syntheses Collective Volume III, pp 167-169, published by John Wiley and Son Inc., New York, 1965. Another method of preparing these compounds comprises the trifluoroacetic acid catalysed addition of the appropriate alcohol $R^1OH$ to a metal isocyanate, as described by S. R. Sandler and W. Karo in Organic Functional Group Preparations, volume 12-II of Organic Chemistry at pages 241-242, published by Academic Press, New York and London, 1971.

The compounds of the invention are useful as herbicides. In another aspect, therefore, the invention provides a process of inhibiting the growth of unwanted plants, which comprises applying to the plants, or to the locus thereof, a phytotoxic amount of a compound of the formula (I) as hereinbefore defined. The amount of the compound to be applied in the process may vary, depending upon the particular compound chosen, and the identity of the plant species whose growth is to be inhibited, but in general amounts from 0.5 to 10 kilograms per hectare will be suitable; in many cases from 3 to 5 kilograms per hectare will be appropriate. The skilled worker in the herbicide art will readily be able to establish appropriate application rates by standard procedures without undue experimentation.

The compounds of the invention may be used to control a variety of unwanted plants. They may be applied to the above-ground parts of unwanted plants (post-emergence application) or they may be applied to the soil to prevent the growth of plants from seeds or germinating seeds present in the soil (pre-emergence application). Compounds of the invention may be used to control various perennial weeds, for example species of the plant genus Cyperus, which is often not controlled by the herbicides commercially available at present. Compounds of the invention may be used, for example, to control broad-leaved weed species growing in cereal crops (e.g. maize, wheat and rice). Examples of compounds which may be used for this purpose include compounds 1 and 10 of Table 1. Compounds of the invention wherein the group Ar is a 4-nitrophenyl group (e.g. Compound 29 of Table 1) tend to have rather a range of herbicidal activity different from that of the other compounds of the invention, being relatively more effective against grass species, and are therefore not generally suitable for use as selective herbicides in cereal crops.

Compounds of the invention also possess activity as plant growth regulators, being capable, for example, when applied at non-phytotoxic rates, of retarding the growth of both monocotyledonous and dicotyledonous plants. They may be useful, for example, in regulating the vegetative growth of cotton.

The compounds used in the process of the invention are preferaby applied in the form of a composition, in which the active ingredient is mixed with a carrier comprising a solid or liquid diluent. In another aspect, therefore, the invention provides a herbicidal composition, comprising as as active ingredient a compound of the formula (I) as hereinbefore defined, in admixture with a solid or liquid diluent. Preferably the composition also comprises a surface-active agent.

The solid compositions of the invention may be for example, in the form of dusting powders, or may take the form of granules. Suitable solid diluents include, for example, kaolin, bentonite, kieselguhr, dolomite, calcium carbonate, talc, powdered magnesia, and Fuller's earth.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecyl-benzenesulphonate, sodium, calcium and ammonium lignosulphonate, butylnaphthalene sulphonate, and a mixture of the sodium salts of diisopropyl- and triisopropyl-naphthalenesulphonic acid. Suitable agents of the non-ionic type include, for example, the condensation products of ethylene oxide with fatty alcohols such as oleyl alcohol and cetyl alcohol, or with alkyl phenols such as octylphenol, nonylphenol, and octylcresol. Other nonionic agents are the partial esters derived from long chain fatty acids and hexitol anhydrides, for example sorbitol monolaurate; the condensation products of the said partial esters with ethylene oxide and the lecithins.

The compositions which are to be used in the form of aqueous solutions, dispersions or emulsions are generally supplied in the form of concentrate containing a high proportion of the active ingredient, the concentrate being diluted with water before use. These concentrates are usually required to withstand storage for prolonged periods and after such storage to be capable of dilution with water in order to form aqueous preparations which remain homogeneous for a sufficient time to enable them to be applied by conventional spray equipment.

The compositions of the invention may contain, in addition to carriers and surface-active agents, various other constituents to increase their usefulness. They may contain, for example, buffering salts to maintain the pH of the composition within a desired range; antifreeze agents, for example urea or propylene glycol; adjuvants, for example, oils and humectants; and sequestrants, for example citric acid and ethylenediaminetetracetic acid, which help to prevent the formation of insoluble precipitates when the compositions are diluted with hard water. Aqueous dispersions may contain anti-settling agents and anti-caking agents.

The compositions may in general contain a dye or pigment to impart a characteristic colour. Agents for increasing viscosity may be added to reduce the formation of fine droplets during spraying, and thereby reduce spray drift. Other additives useful for particular purposes will be known to those skilled in the formulation art.

In general concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many uses contain between 0.01% and 10% and preferably between 0.1% and 1% by weight of the active ingredient.

The compounds of the invention may be used in association (for example in the form of a mixture) with other herbicides and plant growth regulators. The other herbicide may be one chosen to complement the activity of the compound of the invention, so as to produce a mixture useful for complete control of plant growth on a site, or it may be one chosen to increase the usefulness of the compound as a selective herbicide, e.g. by extending the range of weed species controlled without damaging the crop plants. Thus for example, compounds of the invention used for selectively controlling weeds in rice may be mixed with other herbicides already known to be useful for this purpose, for example the herbicides molinate (ethyl ester of 1-hexahydroazepine-1-carbothiolic acid), benthiocarb (s-p-chlorobenzyl ester of N,N-diethyl thiocarbamic acid), chlornitrofen, (4(2,4,6-trichlorophenoxy) nitrobenzene), and chlomethoxynil (2-methoxy-4(2,4-dichlorophenoxy)nitrobenzene).

Other examples of herbicides which may be used in association with compounds of the invention include the following:

A. benzo-2,1,3-thiadiazin-4-one-2,2-dioxides such as 3-isopropylbenzo-2,1,3-thiadiazin-4-one-2,2-dioxide (bentazon);

B. hormone herbicides, particularly the phenoxy alkanoic acids such as 4-chloro-2-methylphenoxy acetic acid (MCPA), 2-(2,4-dichlorophenoxy)propionic acid (dichlorprop), 2,4,5-trichlorophenoxyacetic acid (2,4,5-T), 4-(4-chloro-2-methylphenoxy)butyric acid (MCPB), 2,4-dichlorophenoxyacetic acid (2,4-D), 4-(2,4-dichlorophenoxy)butyric acid (2,4-DB), 2-(4-chloro-2-methylphenoxy)propionic acid (mecoprop), and their derivatives (e.g. salts, esters and amides);

C. 3-[4-(4-halophenoxy)phenyl]-1,1-dialkylureas such as 3-[4-(4-chlorophenoxy)phenyl]-1,1-dimethylurea (chloroxuron);

D. dinitrophenols and their derivatives (e.g. acetates) such as 2-methyl-4,6-dinitrophenol (DNOC), 2-t-butyl-4,6-dinitrophenol (dinoterb), 2-secbutyl-4,6-dinitrophenol (dinoseb) and its ester, dinoseb acetate;

E. dinitroaniline herbicides such as N',N'-diethyl-2,6-dinitro-4-trifluoromethyl-m-phenylenediamine (dinitramine), 2,6-dinitro-N,N-dipropyl-4-trifluoromethylaniline (trifluralin) and 4-methysulphonyl-2,6-dinitro-N,N-dipropylaniline (nitralin);

F. phenylurea herbicides such as N'-(3,4-dichlorophenyl)-N,N-dimethylurea (diuron) and N,N-dimethyl-N'-[3-(trifluoromethyl)phenyl]urea (flumeturon);

G. phenylcarbamoyloxyphenylcarbamates such as 3-[methoxycarbonylamino]phenyl (3-methylphenyl)-carbamate (phenmedipham) and 3-[ethoxycarbonylamino]phenyl phenylcarbamate (desmedipham);

H. 2-phenylpyridazin-3-ones such as 5-amino-4-chloro-2-phenylpyridazin-3-one (pyrazon);

I. uracil herbicides such as 3-cyclohexyl-5,6-trimethyleneuracil (lenacil), 5-bromo-3-sec-butyl-6-methyluracil (bromacil) and 3-t-butyl-5-chloro-6-methyluracil terbacil);

J. triazine herbicides such as 2-chloro-4-ethylamino-6-(i-propylamino)-1,3,5-triazine (atrazine), 2-chloro-4,6-di(ethylamino)-1,3,5-triazine (simazine) and 2-azido-4-(i-propylamino)-6-methylthio-1,3,5-triazine (aziprotryne);

K. 1-alkoxy-1-alkyl-3-phenylurea herbicides such as 3-(3,4-dichlorophenyl)-1-methoxy-1-methylurea (linuron), 3-(4-chlorophenyl)-1-methoxy-1-methylurea (monolinuron) and 3-(4-bromo-4-chlorophenyl)-1-methoxy-1-methylurea (chlorobromuron).

L. thiolcarbamate herbicides such as S-propyl dipropylthiocarbamate (vernolate);

M. 1,2,4-triazin-5-one herbicides such as 4-amino-4,5-dihydro-3-methyl-6-phenyl-1,2,4-triazine-5-one (metamitron) and 4-amino-6-t-butyl-4,5-dihydro-3-methylthio-1,3,4-triazin-5-one (metribuzin);

N. benzoic acid herbicides such as 2,3,6-trichlorobenzoic acid (2,3,6-TBA), 3,6-dichloro-2-methoxybenzoic acid (dicamba) and 3-amino-2,5-dichlorobenzoic acid (chloramben);

O. aniline herbicides such as N-butoxymethyl- -chloro-2',6'-diethylacetanilide (butachlor), the corresponding N-methoxy compound (alachlor), the corresponding N-i-propyl compound (propachlor) and 3',4'-dichloropropionanilide (propanil);

P. dihalobenzonitrile herbicides such as 2,6-dichlorobenzonitrile (dichlobenil), 3,5-dibromo-4-hydroxybenzonitrile (bromoxynil) and 3,5-diiodo-4-hydroxybenzonitrile (ioxynil).

Q. haloalkanoic herbicides such as 2,2-dichloropropionic acid (dalapon), trichloroacetic acid (TCA) and salts thereof;

R. diphenylether herbicides such as 4-nitrophenyl 2-nitro-4-trifluoromethylphenyl ether (fluorodifen), methyl 5-(2,4-dichlorophenoxy)-2-nitrobenzoate (bifenox), 2-nitro-5-(2-chloro-4-trifluoromethylphenoxy)-benzoic acid, 2-chloro-4-trifluoromethylphenyl 3-ethoxy-4-nitrophenyl ether and the compounds of European Patent Specification Publication No. 3416 (the disclosure of which Specification is incorporated herein by reference); and S. miscellaneous herbicides including N,N-dimethyldiphenylacetamide (diphenamid), N-(1-naphthyl)phthalamic acid (naptalam) and 3-amino-1,2,4-triazole.

T. bipyridylium herbicides such as those in which the active entity is the 1,1'-dimethyl-4,4'-dipyridiylium ion (paraquat) and those in which the active entity is the 1,1'-ethylene-2,2'-dipyridylium ion (diquat).

U. Aryloxyphenoxypropionic acids and their derivatives (salts, esters, amides, and the like).

Examples of such acids are:

2-[4-(5-trifluoromethylpyridyl-2-oxy)phenoxy]propionic acid.

2-[4-(4-trifluoromethylphenoxy)phenoxy]propionic acid.

2-[4-(2,4-dichlorophenoxy)phenoxy]propionic acid.
2-[4-(6-chlorobenzoxazolyl-2-oxy)phenoxy]propionic acid
4-methyl-4-(4-trifluoromethylphenoxy)phenoxybut-2-enoic acid.

V. Cyclohexanedione herbicides, for example alloxydimsodium (methyl 4-hydroxy-6,6-dimethyl-2-oxo-3-(1-([2-propenyloxy]imino)butyl)-3-cyclohexen-1-carboxylate sodium salt and sethoxydim having the following structure:

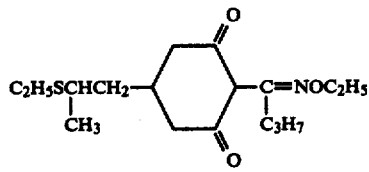

The compounds of the invention may also be used as safening agents (i.e. herbicide "antidotes"); that is to say, they can be mixed with other herbicides to improve the selectivity of the other herbicide as between the crop plant and weeds associated therewith.

The invention is illustrated by the following Examples, in which unless otherwise stated all parts are by weight and all temperatures in degrees Centigrade.

EXAMPLE 1

This Example illustrates the preparation of compound no 3 of Table 1.

A solution of 2-chlorobenzenesulphonylisocyanate (6.95 g) in dry dichloromethane was added to a solution of methyl carbamate (2.41 g) in dry dichloromethane (30 ml). A few crystals of 4-dimethylaminopyridine were added and the mixture stirred at room temperature for 6 hours. The mixture was then left for 48 hours and then stirred for another 4 hours. Removal of the solvent under reduced pressure gave a white solid, which was recrystallised from a mixture of equal volumes of dichloromethane and carbon tetrachloride to give the required compound (7.21 g) with a melting point of 144°-146° C. The structure was confirmed by the infrared and nuclear magnetic resonance spectra of the compound and by elemental analysis.

EXAMPLE 2

This Example illustrates a preparation of N (4-fluorobenzenesulphonyl)-N'-ethoxycarbonylurea (Compound No 30 of Table 1). Sodium hydride (0.45 g of 80% material) was added to a solution of 4-fluorobenzenesulphonamide (2.6 g) in dry dimethylformamide (40 ml). When the effervescence had ceased, ethoxycarbonylisocyanate (1.5 ml) was added to the suspension, giving an immediate solution. After 60 minutes, chromatography showed that reaction was not complete, and a further amount (1 ml) of ethoxycarbonylisocyanate was added. After 5 minutes, thin-layer chromatography showed that no starting material was present. The solution was poured into water, acidified with 2 M hydrochloric acid, and extracted twice with ethyl acetate. The extract was washed with water, and then extracted twice with saturated sodium bicarbonate solution. The sodium bicarbonate solution was acidified with concentrated hydrochloric acid, to give a white solid (3.7 g) with a melting point of 167° C., identified as the required compound.

EXAMPLE 3

This Example illustrates a preparation of N (2-methoxycarbonylbenzenesulphonyl)-N'-ethoxycarbonylurea (Compound No 10 of Table 1)

2-Methoxycarbonylbenzenesulphonamide (2.15 g) was suspended in dichloromethane (20 ml) and ethoxycarbonylisocyanate (1.4 g) added. The solution was heated to reflux and then allowed to cool before addition of triethylamine (1.3 g). After the initial evolution of heat had subsided, the pale yellow solution was heated under reflux for 3.5 hours. The solution was cooled and extracted with 2 M hydrochloric acid (25 ml) and the aqueous layer washed with chloroform (50 ml). The combined organic phases were dried (MgSO₄) and evaporated. The solid residue was recrystallised twice from a mixture of dichloromethane and petroleum (b.p. 60°-80°) giving the product (1.9 g). The compound had a melting point of 158°-160° with a change in form at about 100° C. due to loss of dichloromethane present as solvent of crystallisation.

EXAMPLE 4

This Example illustrates the herbicidal properties of compounds of Table 1. The compounds were submitted to herbicide tests as described below.

Each compound was formulated for test by mixing an appropriate amount of it with 5 ml of an emulsion prepared by diluting 160 ml of a solution containing 21.8 grams per liter of Span 80 and 78.2 grams per liter of Tween 20 in methylcyclohexanone to 500 ml with water. Span 80 is a Trade Mark for a surface-active agent comprising sorbitan monolaurate. Tween 20 is a Trade Mark for a surface-active agent comprising a condensate of 20 molar proportions of ethylene oxide with sorbitan monolaurate. The mixture of the compound and the emulsion was then shaken with glass beads and diluted to 40 ml with water. The spray composition so prepared was sprayed on to young pot plants (post-emergence test) of the species named in Table 2 below, at a rate equivalent to 1000 liters per hectare. Damage to plants was assessed 14 days after spraying by comparison with untreated plants, on a scale of 0 to 5 where 0 is 0 to 20% damage and 5 is complete kill. In the table of results, a dash (-) means that no test was made.

A test was also carried out to detect pre-emergence herbicidal activity. Seeds of the test species were placed on the surface of fibre trays of soil and were sprayed with the compositions at the rate of 1000 liters per hectare. The seeds were then covered with further soil. Three weeks after spraying, the seedlings in the sprayed fibre trays were compared with the seedlings in unsprayed control trays, the damage being assessed on the same scale of 0 to 5.

The results of the tests are given in Table 2 below.

TABLE 2

| COMPOUND NO | RATE OF APPLICATION kg/ha | PRE- OR POST-EMERGENCE APPLICATION | TEST PLANTS | | | | | | | | | | |
|---|---|---|---|---|---|---|---|---|---|---|---|---|---|
| | | | Sb | Rp | Ct | Sy | Mz | Ww | Rc | Sn | Ip | Am | Pi | Ca |
| 1 | 5.0 | Pre | 4 | 5 | 3 | 2 | 1 | 0 | 0 | 5 | 2 | 4 | 4 | — |
| | | Post | 4 | 4 | 2 | 4 | 0 | 1 | 1 | 4 | 2 | 4 | 4 | — |

TABLE 2-continued

| 2 | 5.0 | Pre  | 2 | 2 | 0 | 0 | 0 | 0 | 0 | 3 | 0 | 0 | — | — |
|   |     | Post | 4 | 4 | 1 | 3 | 2 | 1 | 2 | 4 | 0 | 4 | — | 4 |

| COMPOUND NO | RATE OF APPLICATION kg/ha | PRE- OR POST-EMERGENCE APPLICATION | TEST PLANTS | | | | | | | | | | | |
|---|---|---|---|---|---|---|---|---|---|---|---|---|---|---|
| | | | Po | Xs | Ab | Cv | Ot/Av | Dg | Pu | St | Ec | Sh | Ag | Cn |
| 1 | 5.0 | Pre  | 5 | 4 | 4 | — | 0 | 4 | 1 | 2 | 2 | 0 | 2 | 4 |
|   |     | Post | — | 4 | 4 | 5 | 0 | 3 | 1 | 2 | 2 | 0 | 0 | 4 |
| 2 | 5.0 | Pre  | 1 | 0 | 0 | — | 0 | 0 | 0 | 2 | 0 | 0 | 1 | 0 |
|   |     | Post | 3 | 1 | 2 | 2 | 0 | 4 | 0 | 5 | 5 | 3 | 0 | 1 |

Names of test plants in Table 2
Sb: Sugar beet
Rp: Rape
Ct: Cotton
Sy: Soya Bean
Mz: Maize
Ww: Winter wheat
Rc: Rice
Sn: *Senecio vulgaris*
Ip: *Ipomoea purpurea*
Am: *Amaranthus retroflexus*
Pi: *Polygonum aviculare*
Ca: *Chenopodium album*
Po: *Portulaca oleracea*
Xs: *Xanthium spinosum*
Ab: *Abutilon theophrasti*
Cv: *Convolvulus arvensis*
Ot/Av: Oats (cultivated in pre-emergence test and *Avena fatua* (wild oats) in post-emergence test).
Dg: *Digitaria sanguinalis*
Pu: *Poa annua*
St: *Setaria viridis*
Ec: *Echinochloa crus-galli*
Sh: *Sorghum halepense*
Ag: *Agropyron repens*
Cn: *Cyperus rotundus*

EXAMPLE 5

This Example illustrates the herbicidal properties of further compounds of Table 1. The compounds were submitted to herbicidal tests as described below. Each compound was formulated for test by mixing an appropriate amount of it with 1.8 ml of a solution comprising a mixture of 1 part of Span 80 with 1 part of Tween 20 dissolved in methylcyclohexanone, the concentration of the solution being 10 grams of mixture per 100 ml of methylcyclohexanone. Span 80 is a Trade Mark for a surface-active agent comprising sorbitan monolaurate. Tween 80 is a Trade Mark for a surface-active agent comprising a condensate of 20 molar proportions of ethylene oxide with sorbitan monolaurate. The mixture of the test compound and the methylcyclohexanone solution was then shaken with glass beads and diluted to 45 ml with water. The spray composition so prepared was sprayed on to young pot plants (post-emergence test) of the species named in Table 3 below, at a rate equivalent to 1000 liters per hectare. Damage to plants was assessed 14 days after spraying by comparison with untreated plants, on a scale of 0 to 5 where 0 is 0 to 20% damage and 5 is complete kill. In the table of results a dash (-) means that no test was made.

A test was also carried out to detect pre-emergence herbicidal activity. Seeds of the test species were placed on the surface of plastic trays of soil and were sprayed with the compositions at the rate of 1000 liters per hectare. The seeds were then covered with further soil. Three weeks after spraying, the seedlings in the sprayed trays were compared with the seedlings in unsprayed control trays, the damage being assessed on the same scale of 0 to 5. The results are given in Table 3 below:

TABLE 3

| COMPOUND NUMBER | RATE OF APPLICATION kg/ha | PRE- OR POST-EMERGENCE APPLICATION | TEST PLANTS | | | | | | | | | | | | | | | | | | | | | | | | |
|---|---|---|---|---|---|---|---|---|---|---|---|---|---|---|---|---|---|---|---|---|---|---|---|---|---|---|---|
| | | | Sb | Rp | Ct | Sy | Mz | Ww | Rc | Sn | Ip | Am | Pi | Ca | Ga | Xs | Ab | Cs | Av | Dg | Al | St | Ec | Sh | Ag | Cn |
| 5 | 5.0 | Pre | 3 | 2 | 1 | 0 | 0 | 0 | 1 | 2 | 0 | 1 | 0 | 1 | 0 | 0 | 2 | 0 | 0 | 1 | 0 | 0 | 0 | 0 | 0 | 0 |
| | | Post | 1 | 1 | 0 | 0 | 0 | 0 | 0 | 0 | 0 | 0 | 0 | 1 | 1 | 0 | 0 | 0 | 0 | 1 | 0 | 3 | 2 | 0 | 5 | 2 |
| 6 | 5.0 | Pre | 3 | 3 | 2 | 2 | 2 | 4 | 4 | 2 | 2 | 0 | 0 | 4 | 0 | 0 | 0 | 0 | 0 | 2 | 0 | 0 | 2 | 1 | 5 | 0 |
| | | Post | 1 | 3 | 1 | 0 | 1 | 0 | 0 | 0 | 0 | 2 | 0 | 0 | 1 | 0 | 0 | 0 | 1 | 0 | 0 | 0 | 2 | 0 | 0 | 0 |
| 7 | 5.0 | Pre | 0 | 3 | 0 | 0 | 0 | 0 | 0 | 2 | 0 | 2 | 0 | 4 | 0 | 0 | 0 | 0 | 0 | 0 | 0 | 0 | 2 | 0 | 0 | 0 |
| | | Post | 0 | 1 | 1 | 0 | 0 | 0 | 0 | 0 | 0 | 1 | 0 | 0 | 0 | 0 | 0 | 0 | 0 | 0 | 0 | 0 | 3 | 0 | 0 | 1 |
| 8 | 5.0 | Pre | 0 | 3 | 0 | 0 | 0 | 1 | 0 | 0 | 0 | 0 | 2 | 4 | 0 | 0 | 0 | 0 | 0 | 0 | 0 | 4 | 1 | 2 | 0 | 0 |
| | | Post | 1 | 0 | 3 | 2 | 1 | 0 | 4 | 0 | 0 | 3 | 3 | 4 | 2 | 3 | 0 | 0 | 3 | 2 | 3 | 4 | 3 | 0 | 1 | 2 |
| 9 | 5.0 | Pre | 0 | 1 | 0 | 3 | 2 | 1 | 1 | 4 | 4 | 4 | 2 | 4 | 3 | 4 | 3 | 3 | 2 | 4 | 3 | 4 | 3 | 2 | 1 | 0 |
| | | Post | 4 | 4 | 3 | 4 | 0 | 1 | 5 | 4 | 4 | 5 | 3 | 4 | 4 | 4 | 4 | 4 | 0 | 4 | 2 | 4 | 4 | 2 | 0 | 0 |
| 10 | 5.0 | Pre | 4 | 5 | 3 | 4 | 2 | 1 | 1 | 4 | 4 | 4 | 3 | 4 | 4 | 4 | 3 | 4 | 3 | 4 | 4 | 4 | 4 | 2 | 0 | 2 |
| | | Post | 4 | 4 | 2 | 3 | 2 | 0 | 5 | 4 | 3 | 5 | 3 | 5 | 4 | 4 | 3 | 3 | 3 | 4 | 4 | 4 | 3 | 1 | 0 | 0 |
| 10 | 2.0 | Pre | 4 | 4 | 3 | 0 | 0 | 0 | 2 | 4 | 3 | 4 | 2 | 3 | 2 | 3 | 3 | 2 | 2 | 3 | 3 | 3 | 3 | 1 | 0 | 1 |
| | | Post | 4 | 4 | 2 | 3 | 0 | 0 | 0 | 3 | 1 | 2 | 0 | 4 | 1 | 3 | 2 | 2 | 0 | 3 | 3 | 2 | 3 | 1 | 0 | 0 |
| 11 | 5.0 | Pre | 3 | 2 | 2 | 0 | 1 | 0 | 2 | 0 | 1 | 3 | 0 | 0 | 1 | 0 | 0 | 0 | 0 | 0 | 0 | 0 | 1 | 0 | 0 | 0 |
| | | Post | 4 | 4 | 0 | 2 | 0 | 0 | 3 | 2 | 0 | 1 | 0 | 1 | 1 | 1 | 1 | 0 | 0 | 2 | 0 | 0 | 3 | 0 | 0 | 0 |
| 12 | 5.0 | Pre | 4 | 4 | 1 | 3 | 2 | 0 | 3 | 4 | 2 | 2 | 3 | 2 | 1 | 2 | 3 | 2 | 1 | 2 | 2 | 2 | 2 | 0 | 0 | 3 |
| | | Post | 1 | 1 | 0 | 1 | 1 | 1 | 0 | 0 | 0 | 0 | 3 | 1 | 1 | 1 | 1 | 1 | 0 | 1 | 1 | 1 | 1 | 1 | 1 | 1 |
| 13 | 5.0 | Pre | 4 | 5 | 1 | 0 | 0 | 2 | 1 | 4 | 3 | 3 | 3 | 2 | 1 | 1 | 2 | 3 | 0 | 2 | 0 | 2 | 2 | 0 | 0 | 0 |
| | | Post | 4 | 2 | 0 | 2 | 2 | 1 | 0 | 0 | 0 | 0 | 3 | 0 | 1 | 0 | 2 | 3 | 0 | 0 | 2 | 0 | 0 | 0 | 0 | 0 |
| 14 | 5.0 | Pre | 3 | 4 | 0 | 2 | 0 | 1 | 2 | 4 | 2 | 4 | 3 | 2 | 4 | 4 | 5 | 3 | 1 | 3 | 3 | 3 | 3 | 0 | 0 | 5 |
| | | Post | 2 | 2 | 2 | 3 | 1 | 2 | 0 | 3 | 2 | 3 | 0 | 3 | 0 | 2 | 5 | 4 | 0 | 0 | 0 | 0 | 0 | 2 | 0 | 4 |
| 15 | 5.0 | Pre | 4 | 4 | 2 | 2 | 0 | 0 | 2 | 2 | 3 | 0 | 2 | 2 | 0 | 0 | 0 | 2 | 0 | 0 | 0 | 0 | 0 | 0 | 1 | 0 |
| | | Post | 5 | 5 | 0 | 1 | 1 | 1 | 3 | 4 | 2 | 4 | 0 | 2 | 2 | 4 | 3 | 3 | 0 | 3 | 2 | 2 | 0 | 0 | 0 | 2 |
| 16 | 5.0 | Pre | 3 | 2 | 2 | 0 | 1 | 0 | 0 | 0 | 0 | 0 | 2 | 0 | 1 | 2 | 0 | 1 | 0 | 1 | 0 | 0 | 0 | 0 | 0 | 0 |
| | | Post | 3 | 3 | 2 | 2 | 1 | 0 | 4 | 4 | 3 | 5 | 3 | 3 | 4 | 3 | 3 | 4 | 2 | 3 | 2 | 3 | 3 | 0 | 0 | 0 |
| 17 | 5.0 | Pre | 3 | 3 | 0 | 2 | 2 | 1 | 0 | 2 | 1 | 0 | 0 | 0 | 0 | 2 | 1 | 0 | 0 | 1 | 1 | 0 | 0 | 0 | 0 | 0 |
| | | Post | 5 | 5 | 4 | 3 | 0 | 0 | 4 | 4 | 3 | 4 | 3 | 3 | 0 | 3 | 4 | 3 | 0 | 3 | 0 | 0 | 0 | 0 | 0 | 0 |
| 18 | 5.0 | Pre | 5 | 5 | 0 | 0 | 0 | 0 | 0 | 0 | 0 | 0 | 0 | 0 | 0 | 0 | 0 | 0 | 0 | 1 | 0 | 0 | 0 | 0 | 0 | 0 |
| | | Post | 3 | 3 | 2 | 2 | 2 | 0 | 2 | 2 | 0 | 0 | 2 | 0 | 0 | 2 | 3 | 2 | 0 | 0 | 0 | 0 | 0 | 0 | 0 | 0 |
| 19 | 5.0 | Pre | 3 | 3 | 0 | 0 | 1 | 0 | 0 | 0 | 0 | 0 | 0 | 0 | 0 | 0 | 0 | 1 | 0 | 0 | 0 | 0 | 0 | 0 | 0 | 0 |
| | | Post | 5 | 2 | 5 | 2 | 0 | 4 | 2 | 4 | 3 | 0 | 3 | 0 | 4 | 4 | 3 | 4 | 0 | 3 | 3 | 4 | 4 | 2 | 0 | 4 |
| 20 | 5.0 | Pre | 3 | 3 | 0 | 1 | 0 | 1 | 1 | 1 | 0 | 1 | 0 | 0 | 0 | 0 | 1 | 0 | 0 | 0 | 1 | 0 | 0 | 0 | 1 | 0 |
| | | Post | 2 | 2 | 0 | 2 | 0 | 0 | 0 | 0 | 0 | 1 | 0 | 0 | 0 | 0 | 0 | 0 | 0 | 0 | 0 | 0 | 0 | 0 | 0 | 0 |
| 21 | 5.0 | Pre | 1 | 3 | 0 | 1 | 0 | 1 | 1 | 1 | 1 | 1 | 0 | 0 | 0 | 0 | 0 | 1 | 0 | 1 | 1 | 0 | 1 | 0 | 0 | 0 |
| | | Post | 3 | 5 | 5 | 4 | 3 | 4 | 4 | 4 | 3 | 4 | 3 | 4 | 4 | 4 | 4 | 4 | 1 | 2 | 3 | 4 | 4 | 2 | 0 | 5 |
| 22 | 5.0 | Pre | 5 | 5 | 2 | 3 | 2 | 3 | 2 | 4 | 2 | 2 | 3 | 0 | 0 | 2 | 4 | 4 | 0 | 2 | 2 | 2 | 3 | 0 | 0 | 4 |
| | | Post | 1 | 4 | 0 | 0 | 0 | 1 | 2 | 0 | 1 | 0 | 2 | 0 | 0 | 1 | 0 | 1 | 1 | 1 | 0 | 1 | 3 | 0 | 0 | 0 |
| 23 | 5.0 | Pre | 1 | 2 | 0 | 1 | 0 | 1 | 0 | 0 | 0 | 0 | 2 | 0 | 1 | 0 | 0 | 0 | 0 | 0 | 1 | 1 | 1 | 1 | 1 | 0 |
| | | Post | 1 | 4 | 4 | 4 | 3 | 4 | 4 | 4 | 4 | 4 | 4 | 4 | 4 | 4 | 4 | 4 | 0 | 4 | 2 | 4 | 4 | 2 | 0 | 0 |
| 24 | 5.0 | Pre | 5 | 5 | 3 | 3 | 2 | 3 | 4 | 5 | 3 | 4 | 3 | 3 | 4 | 4 | 4 | 4 | 0 | 3 | 3 | 3 | 3 | 1 | 3 | 4 |
| | | Post | 4 | 4 | 4 | 1 | 2 | 1 | 2 | 2 | 1 | 3 | 3 | 4 | 3 | 2 | 2 | 3 | 2 | 2 | 2 | 2 | 3 | 1 | 0 | 5 |
| 25 | 5.0 | Pre | 5 | 5 | 4 | 4 | 4 | 4 | 3 | 4 | 4 | 4 | 4 | 4 | 3 | 4 | 4 | 4 | 2 | 3 | 3 | 4 | 5 | 4 | 3 | 4 |
| | | Post | 4 | 4 | 3 | 3 | 3 | 1 | 2 | 4 | 4 | 4 | 4 | 4 | 4 | 3 | 3 | 3 | 0 | 2 | 3 | 2 | 3 | 0 | 0 | 3 |
| 26 | 5.0 | Pre | 3 | 3 | 2 | 2 | 2 | 2 | 2 | 2 | 0 | 3 | 0 | 1 | 3 | 0 | 0 | 0 | 0 | 0 | 2 | 3 | 3 | 0 | 1 | 0 |
| | | Post | 4 | 4 | 1 | 1 | 0 | 1 | 1 | 1 | 3 | 0 | 3 | 0 | 0 | 0 | 0 | 0 | 0 | 0 | 1 | 0 | 0 | 1 | 0 | 1 |
| 27 | 5.0 | Pre | 4 | 0 | 0 | 0 | 0 | 0 | 1 | 1 | 1 | 0 | 0 | 0 | 0 | 0 | 0 | 0 | 0 | 0 | 0 | 0 | 0 | 1 | 0 | 0 |
| | | Post | 4 | 2 | 1 | 2 | 2 | 0 | 3 | 2 | 3 | 0 | 3 | 0 | 0 | 2 | 0 | 0 | 0 | 0 | 1 | 0 | 0 | 4 | 1 | 0 |
| 28 | 5.0 | Pre | 3 | 5 | 2 | 2 | 0 | 5 | 5 | 5 | 1 | 1 | 3 | 0 | 0 | 0 | 3 | 3 | 0 | 2 | 4 | 5 | 4 | 4 | 0 | 1 |
| | | Post | 3 | 5 | 1 | 1 | 0 | 3 | 5 | 2 | 0 | 0 | 3 | 0 | 0 | 3 | 3 | 3 | 1 | 0 | 3 | 2 | 3 | 3 | 1 | 0 |
| 29 | 5.0 | Pre | 1 | 2 | 2 | 1 | 0 | 4 | 0 | 1 | 0 | 0 | 2 | 0 | 3 | 3 | 3 | 3 | 1 | 3 | 2 | 2 | 3 | 4 | 2 | 0 |
| | | Post | 1 | 2 | 2 | 0 | 0 | 4 | 0 | 1 | 0 | 0 | 2 | 0 | 3 | 3 | 3 | 0 | 1 | 3 | 2 | 2 | 3 | 3 | 2 | 0 |

The test species were the same as those in the test described in Example 4 except that *Avena fatua* was used in both the pre- and post-emergence test; *Portulaca oleracea* was replaced by *Galium aparine* (Ga); *Convolvulus arvensis* was replaced by *Cassia obtusifolia* (Co) and *Poa annua* was replaced by *Alopecurus myosuroides* (Al).

EXAMPLE 6

This Example further illustrates the herbicidal properties of Compound No 1 of Table 1. The compound was formulated in the mixture of solvent and surface-active agents described in Example 4 and sprayed at a rate equivalent to 200 liters per hectare. In the post-emergence test the compounds were applied to young pot plants. In the pre-emergence test the seeds of the test plants were sown in plastic seed trays of soil. The soil surface was sprayed with the compound, and then covered with a layer of untreated soil. Damage was assessed 26 days after spraying by comparison with untreated plants, on a scale of 0 to 9 where 0 is 0 to 5% damage and 9=95-100% kill. The results are given in Tables 4 and 5 below:

To: Tomato
Sg: Sorghum
Eh: *Euphorbia heterophylla*
Ip: *Ipomoea purpurea*
Ab: *Abutilon theophrasti*
Se: *Sesbania exaltata*
Si: *Sida Spinosa*
Ds: *Datura stramonium*
Xa: *Xanthium spinosum*
Ec: *Echinochloa crus-galli*
Dg: *Digitaria sanguinalis*
St: *Setaria viridis*
Sh: *Sorghum halepense*
Pm: *Panicum maximum*
Cd: *Cyperus difformis*
Cn: *Cyperus rotundus*

EXAMPLE 7

This Example illustrates the selective herbicidal properties of Compound 1 of Table 1.

A greenhouse test was carried out as follows: Young rice plants (3 to 4 leaves per plant) (two varieties) were transplanted into plastic containers of soil together with

TABLE 4

| TEST NUMBER | RATE OF APPLICATION kg/ha | PRE- OR POST-EMERGENCE APPLICATION | Ww | Br | Pe | Rp | Sb | Lt | Av | Al | Bt | Ag | Ga | Sm | Ca | Pi | Ma | Sp |
|---|---|---|---|---|---|---|---|---|---|---|---|---|---|---|---|---|---|---|
| 1 | 0.5 | Pre | 0 | 0 | 1 | 9 | 9 | 9 | 3 | 3 | 3 | 0 | 5 | 7 | 9 | 9 | 9 | 9 |
|  | 1.0 | Pre | 1 | 1 | 1 | 9 | 9 | 9 | 4 | 2 | 4 | 1 | 7 | 9 | 9 | 9 | 9 | 9 |
|  | 2.0 | Pre | 1 | 2 | 2 | 9 | 9 | 9 | 3 | 5 | 5 | 2 | 7 | 9 | 9 | 9 | 9 | 9 |
| 2 | 0.5 | Post | 0 | 0 | 1 | 9 | 8 | 8 | 1 | 1 | 0 | 0 | 2 | 8 | 6 | 9 | 8 | 9 |
|  | 1.0 | Post | 0 | 0 | 0 | 9 | 9 | 8 | 1 | 1 | 1 | 1 | 3 | 8 | 7 | 9 | 8 | 9 |
|  | 2.0 | Post | 0 | 0 | 1 | 9 | 9 | 9 | 1 | 2 | 2 | 1 | 7 | 9 | 9 | 9 | 9 | 9 |

TABLE 5

| TEST NUMBER | RATE OF APPLICATION kg/ha | PRE- OR POST-EMERGENCE APPLICATION | Mz | Rc | Sy | Ct | To | Sg | Eh | Ip | Ab | Se | Si | Ds | Xa | Ec | Dg | St | Sh | Pm | Cd | Cn |
|---|---|---|---|---|---|---|---|---|---|---|---|---|---|---|---|---|---|---|---|---|---|---|
| 1 | 0.25 | Pre | 0 | 0 | 0 | 2 | 7 | 1 | 1 | 0 | — | 0 | 0 | 3 | 0 | 1 | 1 | 1 | 4 | 2 | — | — |
|  | 0.50 | Pre | 0 | 0 | 0 | 5 | 8 | 3 | 1 | 0 | — | 1 | 6 | 5 | 2 | 1 | 1 | 2 | 5 | 4 | — | — |
|  | 1.0 | Pre | 1 | 1 | 0 | 7 | 8 | 6 | 1 | 2 | — | 5 | 7 | 8 | 6 | 5 | 4 | 4 | 6 | 7 | — | — |
| 2 | 0.5 | Post | 0 | 1 | 1 | 3 | 5 | 3 | 3 | 0 | 6 | 7 | 4 | 7 | 9 | 0 | 0 | 0 | 0 | 0 | — | — |
|  | 1.0 | Post | 0 | 1 | 0 | 2 | 6 | 3 | 5 | 0 | 7 | 9 | 6 | 7 | 9 | 1 | 0 | 0 | 1 | 0 | 4 | 1 |
|  | 2.0 | Post | 0 | 1 | 4 | 4 | 6 | 2 | 6 | 2 | 8 | 9 | 7 | 8 | 9 | 1 | 0 | 1 | 2 | 2 | 6 | 4 |

The test species in Table 4 were as follows:
WW: Winter wheat
Br: Barley
Pe: Pea
Rp: Oil-seed rape
Sb: Sugar beet
Lt: Lettuce
Av: *Avena fatua*
Al: *Alopecurus myosuroides*
Bt: *Bromus tectorum*
Ag: *Agropyron repens*
Ga: *Galium aparine*
Sm: *Stellara media*
Ca: *Chenopodium album*
Pi: *Polygonum aviculare*
Ma: *Tripleurospermum maritimum inodorum*
Sp: *Sinapis alba*
The test species in Table 5 were as follows:
Mz: Maize
Rc: Rice
Sy: Soya Bean
Ct: Cotton young weed plants of the species *Cyperus serotinus* (Cx) and *Eleocharis acicularis* (Ea). Three days later, chitted seeds of *Echinochloa crus-galli* (Ec) and *Cyperus difformis* (Cd) were sown at a shallow depth. After two more days, the soil was saturated with water and plants of *Salvinia auriculata* were laid on the wet soil surface. The compound, formulated as in Example 4, was then sprayed on to the containers. Damage to the plants was assessed 26 days after spraying, on the scale of 0–9 used in previous Examples. The water-level was gradually raised to 3 cm above the soil surface during the test, and then kept constant. The results are given in Table 6 below:

TABLE 6

| Rate of Application kg/ha | TEST PLANTS | | | | | |
|---|---|---|---|---|---|---|
|  | Rice 1 | Rice 2 | Ec | Cd | Sv | Cx | Ea |
| 0.5 | 0 | 0 | 4 | 4 | 8 | 7 | 0 |
| 1.0 | 0 | 1 | 4 | 4 | 8 | 8 | 1 |
| 2.0 | 1 | 1 | 5 | 7 | 9 | 8 | 2 |

We claim:

1. Sulphonyl urea compounds of the formula (I)

$$ArSO_2NHCONHY \quad (I)$$

wherein Ar is a phenyl ring optionally bearing from one to five substituents each of which may be fluoro-, bromo-, or chloro-alkyl of 1 to 4 carbon atoms other than trifluoromethyl; alkylsulphinyl of 1 to 4 carbon atoms; amino; mono- or di-alkylamino in which the alkyl groups each have from 1 to 4 carbon atoms; carbamoyl optionally substituted by one or two methyl or ethyl groups; carboxyl and salts thereof; or alkoxycarbonyl of 2 to 5 carbon atoms, and Y is a group $-CO_2R^1$ wherein $R^1$ is an alkyl group of 1 to 6 carbon atoms or an alkenyl or alkynyl group of 2 to 6 carbon atoms or a phenyl group; and salts thereof.

2. Compounds as claimed in claim 1 wherein Ar is a phenyl ring substituted in the 2-position.

3. Compounds as claimed in claim 1 wherein Ar is a phenyl ring substituted in both the 2- and the 6-position.

4. Compounds as claimed in claim 1 wherein the group Ar is a phenyl ring containing at least one chloromethyl, bromomethyl, methylsulphinyl, amino, methylamino, dimethylamino, carbamoyl, methoxycarbonyl or carboxy substituent.

5. Compounds as claimed in claim 1 wherein the group Y is a $-CO_2R^1$ group in which $R^1$ is an alkyl group of 1 to 3 carbon atoms or an allyl group.

6. A compound according to claim 1 wherein Ar is a phenyl ring carrying a 2-methoxycarbonyl group and Y is an ethoxycarbonyl group.

7. A process of inhibiting the growth of plants, which comprises applying to the plants, or to the locus thereof, a phytotoxic amount of a compound of formula (I) as defined in claim 1.

8. A herbicidal composition, comprising as an active ingredient a compound of the formula (I) as defined in claim 1 in admixture with a carrier comprising a solid or liquid diluent, and optionally further comprising a surface-active agent.

9. A herbicidal composition, comprising as an active ingredient a compound of the formula (I) as defined in claim 1, in admixture with at least one other herbicide.

10. Sulphonyl urea compounds of the formula (I)

$$ArSO_2NHCONHY \quad (I)$$

wherein Ar is a phenyl ring bearing a substituent in the 2-position and optionally bearing further substituents, each substituent being a halogen atom, an alkyl group of 1 to 4 carbon atoms, an alkoxy group of 1 to 4 carbon atoms, an alkylthio group of 1 to 4 carbon atoms, a fluoro-, bromo-, or chloro-alkyl group of 1 to 4 carbon atoms, cyano, nitro, or an alkylsulphonyl group of 1 to 4 carbon atoms and Y is a group $-CO_2R^1$ wherein $R^1$ is an alkyl group of 1 to 6 carbon atoms or an alkenyl or alkynyl group of 2 to 6 carbon atoms or a phenyl group, provided that $R^1$ is not a methyl group when Ar is a 2-chlorophenyl, 2-methylphenyl, 2-methoxyphenyl, or 2-nitrophenyl group; and salts thereof.

11. Compounds as claimed in claim 10 wherein Ar is a phenyl ring substituted in both the 2- and the 6-position.

12. Compounds as claimed in claim 10 wherein the group Ar is a 2-methylphenyl, 2-methoxyphenyl, 2-methylthiophenyl, 2-chlorophenyl or 2-trifluoromethylphenyl groups.

13. Compounds as claimed in claim 10 wherein the group Y is a $-CO_2R^1$ group in which $R^1$ is an alkyl group of 1 to 3 carbon atoms or an allyl group.

14. A compound as claimed in claim 10 wherein Ar is a 2-trifluoromethyl-phenyl or 2-chlorophenyl group and Y is an ethoxycarbonyl group.

15. A process inhibiting the growth of plants, which comprises applying to the plants, or to the locus thereof, a phytotoxic amount of a compound of formula (I) as defined in claim 10.

16. A herbicidal composition, comprising as an active ingredient a compound of the formula (I) as defined in claim 10 in admixture with a carrier comprising a solid or liquid diluent, and optionally further comprising a surface-active agent.

17. A herbicidal composition, comprising as an active ingredient a compound of the formula (I) as defined in claim 10, in admixture with at least one other herbicide not being a thiolcarbamate, thiolcarbamate sulphoxide, or haloacetanilide herbicide.

* * * * *